(12) United States Patent  (10) Patent No.: US 8,017,311 B2
Brockbank et al.  (45) Date of Patent: Sep. 13, 2011

(54) METHOD FOR TREATMENT OF CELLULAR MATERIALS WITH SUGARS PRIOR TO PRESERVATION

(75) Inventors: Kelvin G. M. Brockbank, Charleston, SC (US); Lia H. Campbell, Mt. Pleasant, SC (US); Kelly M. Ratcliff, Mt. Pleasant, SC (US); Kristy A. Sarver, Ladson, SC (US)

(73) Assignee: Organ Recovery Systems, Inc., Des Plaines, IL (US)

( * ) Notice: Subject to any disclaimer, the term of this patent is extended or adjusted under 35 U.S.C. 154(b) by 1009 days.

(21) Appl. No.: 11/856,650

(22) Filed: Sep. 17, 2007

(65) Prior Publication Data

US 2008/0070302 A1  Mar. 20, 2008

Related U.S. Application Data

(62) Division of application No. 10/670,724, filed on Sep. 26, 2003, now Pat. No. 7,270,946.

(60) Provisional application No. 60/415,777, filed on Oct. 4, 2002.

(51) Int. Cl.
*A01N 1/00* (2006.01)
(52) U.S. Cl. .................... 435/1.1; 435/1.2; 435/1.3
(58) Field of Classification Search .................. None
See application file for complete search history.

(56) References Cited

U.S. PATENT DOCUMENTS

| | | | |
|---|---|---|---|
| 5,242,792 | A | 9/1993 | Rudolph et al. |
| 5,629,145 | A | 5/1997 | Meryman |
| 5,648,206 | A | 7/1997 | Goodrich et al. |
| 5,827,741 | A | 10/1998 | Beattie et al. |
| 5,955,448 | A | 9/1999 | Calaco et al. |
| 5,962,214 | A | 10/1999 | Fahy et al. |
| 6,127,177 | A | 10/2000 | Toner et al. |
| 6,187,529 | B1 | 2/2001 | Fahy et al. |
| 6,194,137 | B1 | 2/2001 | Kharabadi et al. |
| 6,274,303 | B1 | 8/2001 | Wowk et al. |
| 6,395,467 | B1 | 5/2002 | Fahy et al. |
| 6,740,484 | B1 | 5/2004 | Khirabadi et al. |
| 6,770,478 | B2 | 8/2004 | Crowe et al. |
| 2005/0277107 | A1 | 12/2005 | Toner et al. |

FOREIGN PATENT DOCUMENTS

| | | | |
|---|---|---|---|
| WO | WO 00/64254 | * | 11/2000 |
| WO | WO 02/32225 A2 | | 4/2002 |

OTHER PUBLICATIONS

Masaki et al., "Effect on Rat Kidney Preservation in the Cold of Various Sugars Added to Euro-Collins Solution to Adjust Osmolarity", Transplantation Proceedings 37 (7) : 1623-1625 (2000).*
Taylor et al., "Comparison of Unisol With Euro-Collins Solution as a Vehicle Solution for Cryoprotectants", Transplantation Proceedings 33 : 677-679 (2001).*
Fischer et al., "Raffinose Improves 24-Hour Lung Preservation in Low Potassium Dextran Glucose Solution: A Histologic and Ultrastructural Analysis", Annals of Thoracic Surgery 71 : 1140-1145 (2001).*
Polce et al., "Revival of Spermatozoa after Vitrification and Dehydration at Low Temperatures," Nature, vol. 164, p. 666, Oct. 1949.
Lovelock et al., "Prevention of Freezing Damage to Living Cells by Dimethyl Sulphoxide," Nature, vol. 183, pp. 1394-1395, May 1959.
Brockbank et al., "Synergistic Interaction of Low-Molecular-Weight Polyvinylpyrrolidones with Dimethylsulfoxide During Cell Cryopreservation," Transplantation Proceedings, vol. 25, No. 6, pp. 3189-3191, Dec. 1993.
Song et al., "Vitreous Cryopreservation Maintains the Function of Vascular Grafts,"Nature Biotechnology, vol. 18, pp. 296-299, Mar. 2000.
Crowe et al., "The Role of Vitrification in Anhydrobiosis," Annu. Rev. Physiol., vol. 60, pp. 73-103, 1998.
Potts, "Desiccation Tolerance of Prokaryotes," Microbiological Reviews, vol. 58, No. 4, pp. 755-805, Dec. 1994.
Crowe et al., "Interactions of Sugars with Membranes," Biochimica et Biophysica Acta, vol. 947, pp. 367-384, 1988.
Crowe et al., "Anhydrobiosis," Annu. Rev. Physiol., vol. 54, pp. 579-599, 1992.
Womersley et al., "Inhibition of Dehydration-Induced Fusion between Liposomal Membranes by Carbohydrates as Measured by Fluorescence Energy Transfer," Cryobiology, vol. 23, pp. 245-255, 1986.
De Castro et al., "Anhydrobiotic Engineering," Nature Biotechnology, vol. 18, p0. 473, May 2000.
Eroglu et al., Intracellular Trehalose Improves the Survival of Cryopreserved Mammalian Cells,Nature Biotechnology, vol. 18, pp. 163-167, Feb. 2000.
Beattie et al., "Trehalose: A Cryoprotectant That Enhances Recovery and Preserves Function of Human Pancreatic Islets after Long-Term Storage," Diabetes, vol. 46, pp. 519-523, Mar. 1997.
Acker et al., "Tissue Engineering," Science & Medicine, pp. 126-127, May/Jun. 2000.
Guo et al., "Trehalose Expression Confers Desiccation Tolerance on Human Cells", Nature Biotechnology, vol. 18, pp. 168-170, Feb. 2000.
Gilles et al., "Effect of Compensatory Organic Osmolytes on Resistance to FreezeDrying of L929 Cells and of their Isolated Chromatin," Comparative Biochemistry and Physiology Part A 122: 145-155 (1999).
Scannell et al., "The Regulation of Carbohydrate Metabolism in Animal Cells Growth on Starch and Maltose," Biochemical Society Transactions 8 (5) : 633-4 (1980).
Kim et al., "Cryopreservation of *Taxus chirensis* Suspension Cell Cultures," CryoLetters 22: 43-50 (2001).
Burger et al. "Transport of Some Mono- and Di-Saccharides Into Yeast Cells," Biochemical Journal 71: 235-42 (1959).

* cited by examiner

Primary Examiner — Sandra Saucier
(74) Attorney, Agent, or Firm — Oliff & Berridge, PLC

(57) ABSTRACT

Living cellular material may be preserved by incubating the cellular material in a culture medium containing at least one sugar, particularly for at least three hours, and then subjecting the cellular material to a preservation protocol, such as freezing, vitrification, freeze-drying and desiccation.

20 Claims, 8 Drawing Sheets

METHOD FOR TREATMENT OF CELLULAR MATERIALS WITH SUGARS PRIOR TO PRESERVATION

CROSS-REFERENCE TO RELATED APPLICATIONS

This is a Division of application Ser. No. 10/670,724 filed Sep. 26, 2003, which claims the benefit of U.S. Provisional Application No. 60/415,777 filed Oct. 4, 2002. The disclosure of each of the prior applications is hereby incorporated by reference in its entirety.

The U.S. Government has a paid-up license in this invention and the right in limited circumstances to require the patent owner to license others on reasonable terms as provided by the terms of cooperative agreement No. 70NANB1H3008 awarded by the National Institute of Standards and Technology (NIST).

BACKGROUND OF THE INVENTION

1. Field of Invention

The invention relates to the field of cell, tissue and organ preservation. More specifically, the invention relates to a method for treatment of cellular materials with sugars prior to preservation in an effort to enhance cell survival post-preservation. This is particularly important because the sugars, such as trehalose and sucrose, are not cytotoxic to cells and therefore may not have to be removed before living, natural or man-made cellular materials are transplanted into humans or animals.

2. Description of Related Art

Conventional approaches to cryopreservation that provide the cornerstone of isolated cell storage have not been successfully extrapolated to more complex natural, or engineered, multicellular tissues. Tissues are much more than simple aggregates of various cell types; they have a highly organized, often complex, structure that influences their response to freezing and thawing. Cryopreservation is a complex process of coupled heat and mass transfer generally executed under non-equilibrium conditions. Advances in the field were modest until the cryoprotective properties of glycerol and dimethyl sulfoxide (DMSO) were discovered in the mid 1900's.[1,2] Many other cryoprotective agents (CPAs) have since been identified. Combinations of CPAs may result in additive or synergistic enhancement of cell survival by minimization of intracellular ice during freezing.[3]

Restriction of the amount and size of extracellular ice crystal formation during cryopreservation can be achieved by using high concentrations of CPAs that promote amorphous solidification, known as vitrification, rather than crystallization.[4] Vitrification is a relatively well understood physical process, but its application to the preservation of biological systems has not been without problems, since the high concentrations of CPAs necessary to facilitate vitrification are potentially toxic. To limit toxic effects, it is necessary to use the least toxic CPAs at the lowest concentrations that will still permit glass formation (at cooling rates that are practical for bulky mammalian tissues).[4] Comparison of the effects of vitrification and conventional frozen cryopreservation upon venous contractility demonstrate that vitrification is superior to conventional cryopreservation methods for tissues.[4] However, both vitrification and conventional freezing methods have their place in the cryopreservation of cellular materials.

However, both conventional freezing and vitrification approaches to preservation have limitations. First, both of these technologies require low temperature storage and transportation conditions. Neither can be stored above their glass transition temperature for very long without significant risk of product damage due to ice formation and growth. Both technologies require competent technical support during the rewarming and CPA elution phase prior to product utilization. This is possible in a high technology surgical operating theater but not in a doctor's outpatient office or in third world environments. In contrast, theoretically, a dry product would have none of these issues because it should be stable at room temperature and rehydration should be feasible in a sterile packaging system.

Drying and vitrification have previously been combined for matrix preservation of cardiovascular and skin tissues, but not for live cell preservation in tissues or engineered products. Nature, however, has developed a wide variety of organisms and animals that tolerate dehydration stress by a spectrum of physiological and genetic adaptation mechanisms. Among these adaptive processes, the accumulation of large amounts of disaccharides, especially trehalose and sucrose, is especially noteworthy in almost all anhydrobiotic organisms including plant seeds, bacteria, insects, yeast, brine shrimp, fungi and their spores, cysts of certain crustaceans, and some soil-dwelling animals.[5-7] The protective effects of trehalose and sucrose may be classified under two general mechanisms: (1) "the water replacement hypothesis" or stabilization of biological membranes and proteins by direct interaction of sugars with polar residues through hydrogen bonding, and (2) stable glass formation (vitrification) by sugars in the dry state.

The stabilizing effect of these sugars has also been shown in a number of model systems, including liposomes, membranes, viral particles, and proteins during dry storage at ambient temperatures.[8-10] On the other hand, the use of these sugars in mammalian cells has been somewhat limited, mainly because mammalian cell membranes are believed to be impermeable to disaccharides or larger sugars.[11] For sugars to be effective, it is believed that they need to be present both on the inside and the outside of the cell membrane. Several methods have been developed for loading of sugars in living cells. Recently, a novel, genetically-modified, metal-actuated switchable membrane pore has been used to reversibly permeabilize mammalian cells to sugars with significant post-cryopreservation and, to lesser extent, drying cell survival.[12] Other permeation technologies that have been considered for placing sugars in cells include use of microinjection and thermal shock. The expression of sucrose and trehalose synthase genes and transporters has also been considered as means for delivery of sugars into cells. Introduction of trehalose into human pancreatic islet cells during a cell membrane thermotropic lipid-phase transition, prior to freezing and in the presence of a mixture of 2M DMSO and trehalose, resulted in previously unattainable cell survival rates.[13] This method depends upon suspension of cells in a trehalose solution and either cooling or warming the solution through the thermotropic transition of the cells.[14] Human fibroblast transfection with *E. coli* genes expressing trehalose resulted in retention of viability after drying for up to five days.[15]

SUMMARY OF THE INVENTION

It was found that the incubation of cellular materials under physiological conditions in the presence of low concentrations of sugars resulted in increased cell survival without any need for the metal-actuated switchable membrane pore.

The present application thus provides a method for pretreatment of cellular materials with sugars that enhances the ability of these cellular materials to survive a subsequent preservation procedure. Incubation of cellular materials with sugars under physiological conditions for short periods of time (such as less than 3 hours), with or without simple addition of extracellular sugars just prior to cell preservation, results in few, if any, cells surviving preservation procedures. However, we have discovered that prolonged incubation with sugars under physiological conditions (such as greater than 3 hours) prior to preservation results in cell survival under conditions that would otherwise have resulted in minimal, if any, cell survival.

As used herein, "cellular material" refers to living biological material containing cellular components, whether the material is natural or man-made. Cellular material includes cells, tissues and organs, whether natural or man-made.

As used herein, "preservation protocol" refers to a process for provision of shelf life to a cell containing, living biological material. Preservation protocols include cryopreservation by freezing and vitrification and anhydrobiotic preservation by either freeze-drying or desiccation.

U.S. Pat. No. 6,127,177 to Toner et al. (hereinafter "Toner") describes a preservation method for biological material, comprising reversibly porating cell membranes of the biological material; loading a bio-protective agent having bio-preservation properties, such as non-permeating sugars, to a predetermined intracellular concentration; preparing the bio-protective agent loaded biological material for storage; storing the biological material; recovering the stored biological material from storage; and reversing the cell membrane poration. To reversibly porate the cell membranes, Toner describes the use of a toxin. Toner, which is herein incorporated by reference in its entirety, describes a process that is similar to the process of the present invention, except that in the present invention there is no need to reversibly porate the cell membranes using a toxin. Instead, the cellular material is incubated with sugars for at least three hours.

DETAILED DESCRIPTION OF PREFERRED EMBODIMENTS

Figure 1:
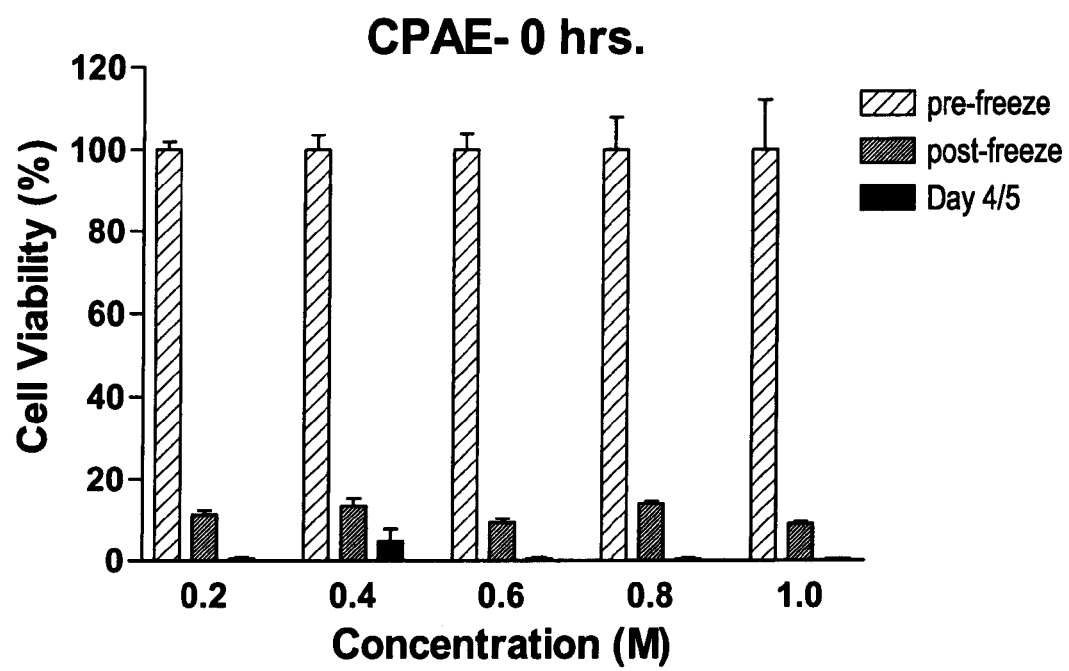
FIG. 1 demonstrates the cell viability before and after freezing where the cell line is not first incubated in a culture medium containing sugar. The legend provided in FIG. 1 applies to FIGS. 2-8, as well.

The present invention is directed to a method for preserving living cellular materials. The method comprises incubating the cellular material in a culture medium containing at least one sugar.

The sugar may be any sugar but is preferably a polysaccharide. As used herein, the term "polysaccharide" refers to a sugar containing more than one monosaccharide unit. That is, the term polysaccharide includes oligosaccharides such as disaccharides and trisaccharides, but does not include monosaccharides. The sugar may also be a mixture of sugars, preferably where at least one of the sugars is a polysaccharide.

Even more preferably, the sugar is a disaccharide or trisaccharide. In embodiments, the disaccharide is trehalose and/or sucrose and the trisaccharide is raffinose. The sugar may also be a combination of trehalose and/or sucrose and/or raffinose and/or other disaccharides or trisaccharides. In the most preferred embodiment, the sugar includes trehalose.

In embodiments of the invention, the culture medium contains from 0.1 to 0.4M sugar, particularly from 0.1 to 0.4M polysaccharide sugar. More preferably, the culture medium contains from 0.1 to 0.3M sugar, particularly from 0.1 to 0.3M polysaccharide sugar.

The culture medium may be any formulation that may be used in the culture of cells, such as Dulbecco's Modified Eagle's Medium (DMEM) and Minimum Essential Medium Eagle (MEME) either with or without serum. In general, the culture medium will be selected based on the cell type. In embodiments, the culture medium may have a composition as listed in Table A.

TABLE A

| Component | Amount (g/L) | DMEM (g/L) | MEME (g/L) |
|---|---|---|---|
| L-Alanine | 0-0.009 | — | 0.0089 |
| L-Arginine·HCl | 0.08-0.2 | 0.084 | 0.126 |
| L-Asparagine·H$_2$O | 0-0.02 | — | 0.015 |
| L-Aspartic Acid | 0-0.02 | — | 0.0133 |
| L-Cystine·2HCl | 0.03-0.07 | 0.0626 | 0.0313 |
| L-Glutamic Acid | 0-0.02 | — | 0.0147 |
| L-Glutamine | 0-0.3 | — | 0.292 |
| Glycine | 0.007-0.04 | 0.03 | 0.0075 |
| L-Histidine·HCl·H$_2$O | 0.04-0.05 | 0.042 | 0.042 |
| L-Isoleucine | 0.05-0.2 | 0.105 | 0.052 |
| L-Leucine | 0.05-0.2 | 0.105 | 0.052 |
| L-Lysine·HCl | 0.07-0.2 | 0.146 | 0.0725 |
| L-Methionine | 0.01-0.04 | 0.03 | 0.015 |
| L-Phenylalanine | 0.03-0.07 | 0.066 | 0.032 |
| L-Proline | 0-0.02 | — | 0.0115 |
| L-Serine | 0.01-0.05 | 0.042 | 0.0105 |
| L-Threonine | 0.04-0.1 | 0.095 | 0.048 |
| L-Tryptophan | 0.009-0.02 | 0.016 | 0.01 |
| L-Tyrosine (L-Tyr·2Na·2H$_2$O in MEME) | 0.03-0.08 | 0.072 | 0.0519 |
| L-Valine | 0.04-0.1 | 0.094 | 0.046 |
| Choline Bitartrate | 0-0.008 | 0.0072 | — |
| Choline Chloride | 0-0.002 | — | 0.001 |
| Folic Acid | 0.0009-0.005 | 0.004 | 0.001 |
| Myo-Inositol | 0.001-0.008 | 0.0072 | 0.002 |
| Niacinamide | 0.0009-0.005 | 0.004 | 0.001 |
| D-Pantothenic Acid Hemicalcium | 0.0009-0.005 | 0.004 | 0.001 |
| Pyridoxal·HCl | 0.0009-0.005 | 0.004 | 0.001 |
| Riboflavin | 0.00009-0.0005 | 0.0004 | 0.0001 |
| Thiamine·HCl | 0.0009-0.005 | 0.004 | 0.001 |
| Calcium Chloride·2H$_2$O | 0.2-0.3 | 0.265 | 0.265 |
| Ferric Nitrate | 0-0.0002 | 0.0001 | — |
| Magnesium Sulfate (anhydrous) | 0.09-0.1 | 0.09767 | 0.09767 |
| Potassium Chloride | 0.3-0.5 | 0.4 | 0.4 |
| Sodium Chloride | 6.0-7.0 | 6.4 | 6.8 |
| Sodium Phosphate Monobasic (anhydrous) | 0.1-0.2 | 0.109 | 0.122 |
| Succinic Acid | 0-0.08 | 0.075 | — |
| Sodium Succinate·6H$_2$O | 0-0.2 | 0.1 | — |
| Sodium Pyruvate | 0-0.2 | 0.11 | — |
| Glucose | 0.5-2.0 | 1.0 | 1.0 |
| Phenol Red·Na | 0-0.02 | 0.0093 | 0.011 |

To achieve the positive effects of incubation, the cellular material is generally incubated in the sugar-containing culture medium for at least three hours. However, it may be possible to achieve the positive effects with shorter periods of incubation. Preferably, the cellular material is incubated for at least 6 hours, more preferably for at least 12 hours, even more preferably for at least 18 hours, even more preferably for at least 24 hours, even more preferably for at least 48 hours and even more preferably for at least 72 hours. In general, the cellular material may be incubated for 3 to 120 hours and can even be incubated for a longer period of time, such as by incorporation of the sugar into the cell culture medium used to maintain the cells. Preferably, the cellular material is incubated for from 6-72 hours, more preferably from 12-48 hours, even more preferably from 18-46 hours and even more preferably from 18-36 hours.

After incubation in the culture medium, the cellular material undergoes a preservation protocol. This preservation protocol may comprise cooling the cellular material and/or drying the cellular material. For example, the cellular material may be preserved by freezing, vitrifying, freeze-drying and desiccating. Protocols for preserving cellular material by these techniques are described in the following patents and publications: U.S. Pat. No. 6,395,467 to Fahy et al.; U.S. Pat. No. 6,274,303 to Wowk et al.; U.S. Pat. No. 6,194,137 to Khirabadi et al.; U.S. Pat. No. 6,187,529 to Fahy et al.; U.S. Pat. No. 6,127,177 to Toner et al.; U.S. Pat. No. 5,962,214 to Fahy et al.; U.S. Pat. No. 5,955,448 to Calaco et al.; U.S. Pat. No. 5,827,741 to Beattie et al.; U.S. Pat. No. 5,648,206 to Goodrich et al.; U.S. Pat. No. 5,629,145 to Meryman; U.S. Pat. No. 5,242,792 to Rudolph et al.; and WO 02/32225 A2, which corresponds to U.S. patent application Ser. No. 09/691,197 to Khirabadi et al., which are each hereby incorporated in their entirety by reference.

In cryopropreservation, before freezing or vitrifying the cellular material, the cellular material is brought into contact with a cryoprotectant-containing composition. Thus, in embodiments where the preservation protocol is a cryopreservation protocol, after incubating the cellular material in a culture medium containing at least one sugar, the cellular material may be brought into contact with a cryoprotectant-containing composition prior to freezing or vitrifying the cellular material.

As used herein, the term "cryoprotectant" means a chemical that minimizes ice crystal formation in a cellular material when the cellular material is cooled to subzero temperatures and results in an increase in viability after warming, in comparison to the effect of cooling without cryoprotectant. Cryoprotectants include, but are not limited to, acetamide, agarose, alginate, alanine, albumin, ammonium acetate, anti-freeze proteins, butanediols (such as 2,3-butanediol), chondroitin sulfate, chloroform, choline, cyclohexanediols, cyclohexanediones, cyclohexanetriols, dextrans, diethylene glycol, dimethyl acetamide, dimethyl formamide (such as n-dimethyl formamide), dimethyl sulfoxide, erythritol, ethanol, ethylene glycol, ethylene glycol monomethyl ether, formamide, glucose, glycerol, glycerophosphate, glyceryl monoacetate, glycine, glycoproteins, hydroxyethyl starch, inositol, lactose, magnesium chloride, magnesium sulfate, maltose, mannitol, mannose, methanol, methoxy propanediol, methyl acetamide, methyl formamide, methyl ureas, methyl glucose, methyl glycerol, phenol, pluronic polyols, polyethylene glycol, polyvinylpyrrolidone, proline, propanediols (such as 1,2-propanediol and 1,3-propanediol), pyridine N-oxide, raffinose, ribose, serine, sodium bromide, sodium chloride, sodium iodide, sodium nitrate, sodium nitrite, sodium sulfate, sorbitol, sucrose, trehalose, triethylene glycol, trimethylamine acetate, urea, valine and xylose. Other cryoprotectants that may be used in the present invention are described in U.S. Pat. No. 6,395,467 to Fahy et al.; U.S. Pat. No. 6,274,303 to Wowk et al.; U.S. Pat. No. 6,194,137 to Khirabadi et al.; U.S. Pat. No. 6,187,529 to Fahy et al.; U.S. Pat. No. 5,962,214 to Fahy et al.; U.S. Pat. No. 5,955,448 to Calaco et al.; U.S. Pat. No. 5,629,145 to Meryman; and/or WO 02/32225 A2, which corresponds to U.S. patent application Ser. No. 09/691,197 to Khirabadi et al.

In a preferred embodiment of the invention, the cryoprotectant-containing composition contains at least one sugar. The sugar may be a mixture of sugars and preferably contains at least one polysaccharide, particularly a disaccharide, such as trehalose and/or sucrose, and/or a trisaccharide, such as raffinose. The composition preferably contains from 0.1 to 2.0M sugar, more preferably from 0.2 to 0.6M sugar. The cryoprotectant-containing composition may be the sugar-containing culture medium that was used in the incubation. Optionally, additional sugar and/or other cryoprotectants may be added to this culture medium prior to freezing or vitrifying the cellular material.

EXAMPLES

A bovine pulmonary artery endothelial cell line, CPAE, is used for these experiments. Cells are plated the night before in 96-well microtiter plates at 20,000 cells/well, then exposed to 0.2M trehalose in Dulbecco's Modified Eagle's Medium (DMEM) at 37° C. for 0, 3, 6, 12, 18, 24, 48 and 72 hours.

Following exposure and prior to freezing, cell viability is determined using the non-invasive metabolic indicator alamarBlue (Trek Diagnostics). Thus, after exposure to DMEM containing trehalose for the above-identified time periods, a volume of 20 µl of alamarBlue is added to cells in 200 µl of DMEM (10% FCS) and the plate is allowed to incubate at 37° C. for an additional three hours. The plate is read using a fluorescent microplate reader (Molecular Dynamics) at an excitation wavelength of 544 nm and an emission wavelength of 590 nm. The alamarBlue assay is chosen because it is non-toxic and can be used to assess the viability of the cells without damage. Thus, cell viability can be confirmed and then the cells can be immediately frozen in the plate.

Figure 2:
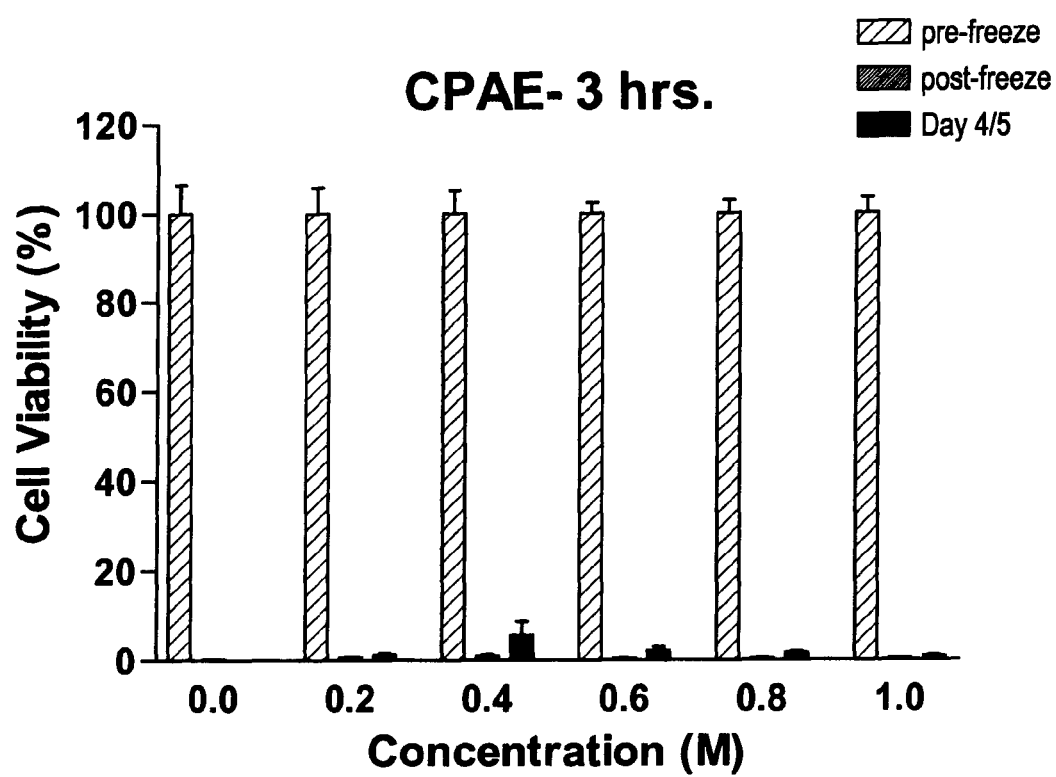
FIG. 2 demonstrates the cell viability before and after freezing where, prior to freezing, the cell line is incubated for three hours in a culture medium containing 0.2M trehalose.
Figure 3:
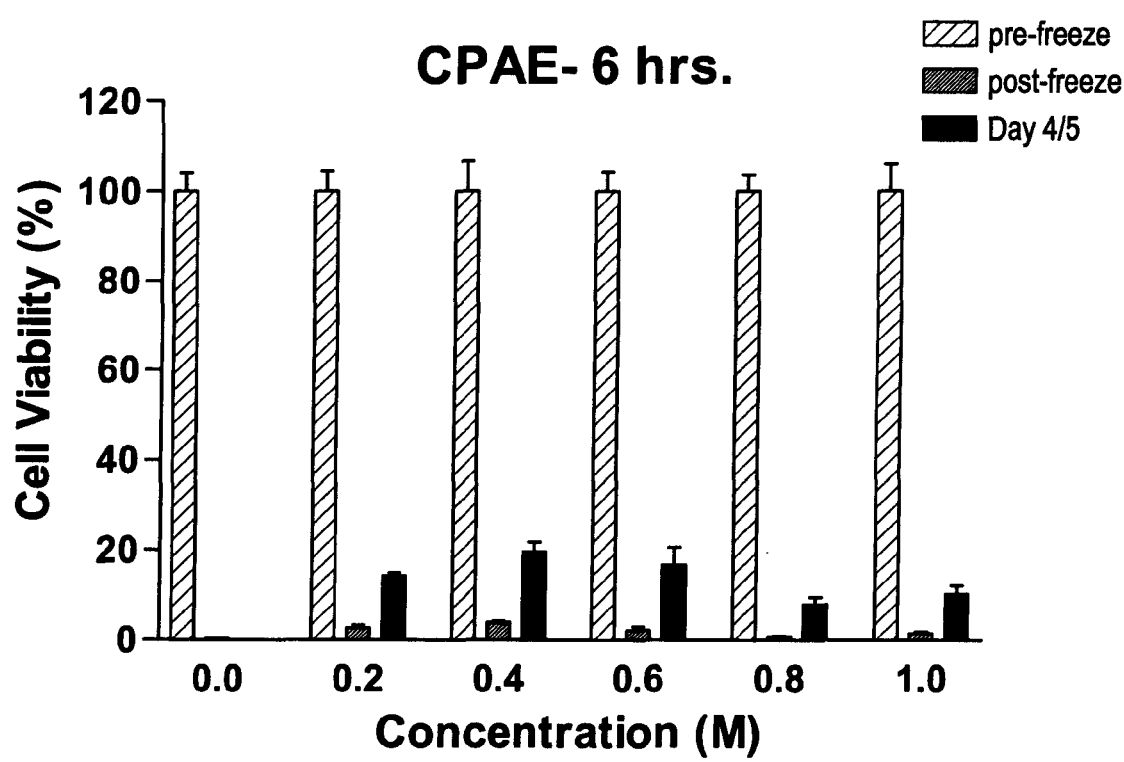
FIG. 3 demonstrates the cell viability before and after freezing where, prior to freezing, the cell line is incubated for six hours in a culture medium containing 0.2M trehalose.
Figure 4:
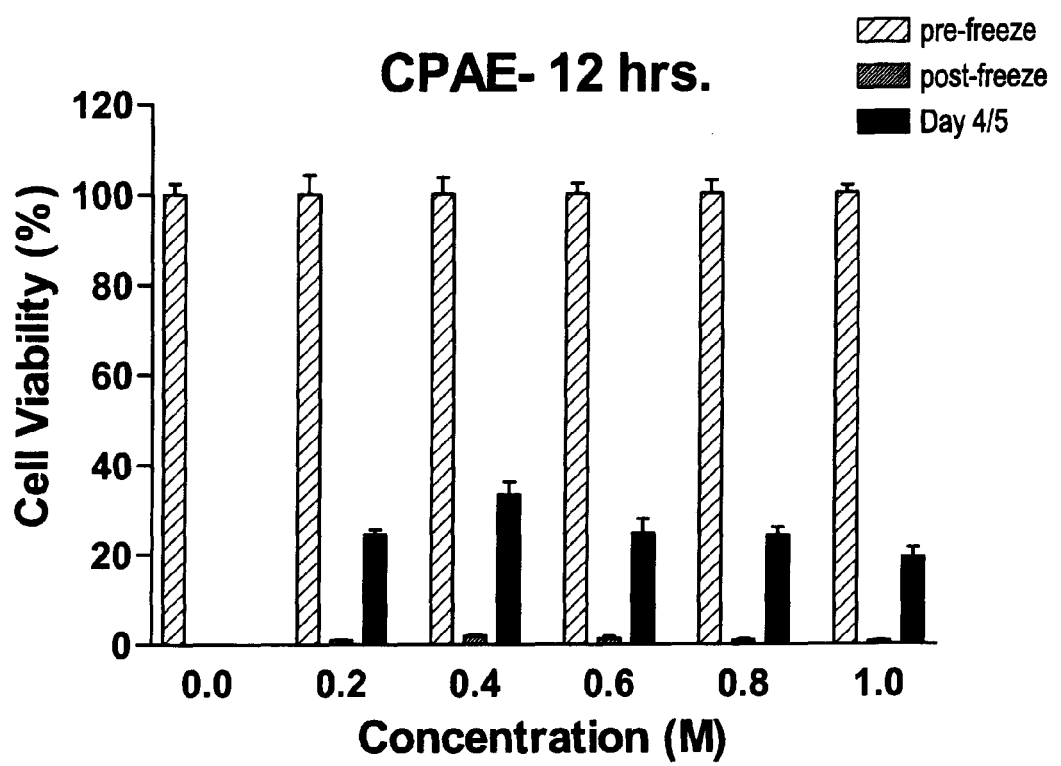
FIG. 4 demonstrates the cell viability before and after freezing where, prior to freezing, the cell line is incubated for 12 hours in a culture medium containing 0.2M trehalose.
Figure 5:
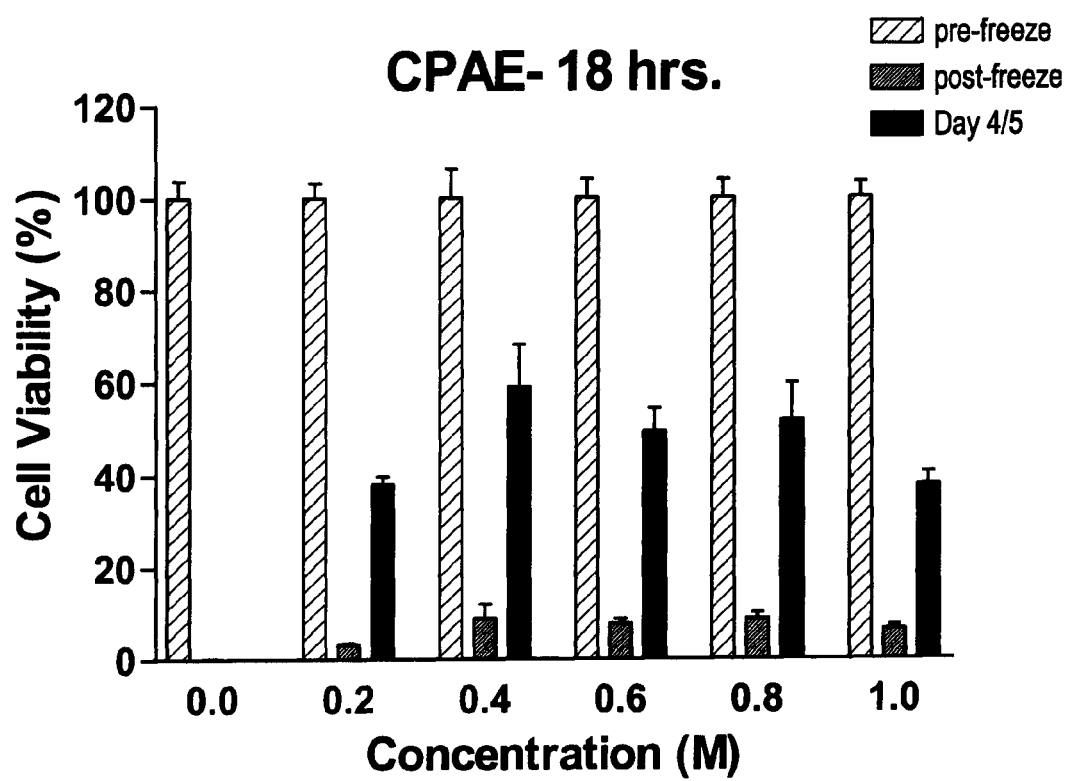
FIG. 5 demonstrates the cell viability before and after freezing where, prior to freezing, the cell line is incubated for 18 hours in a culture medium containing 0.2M trehalose.
Figure 6:
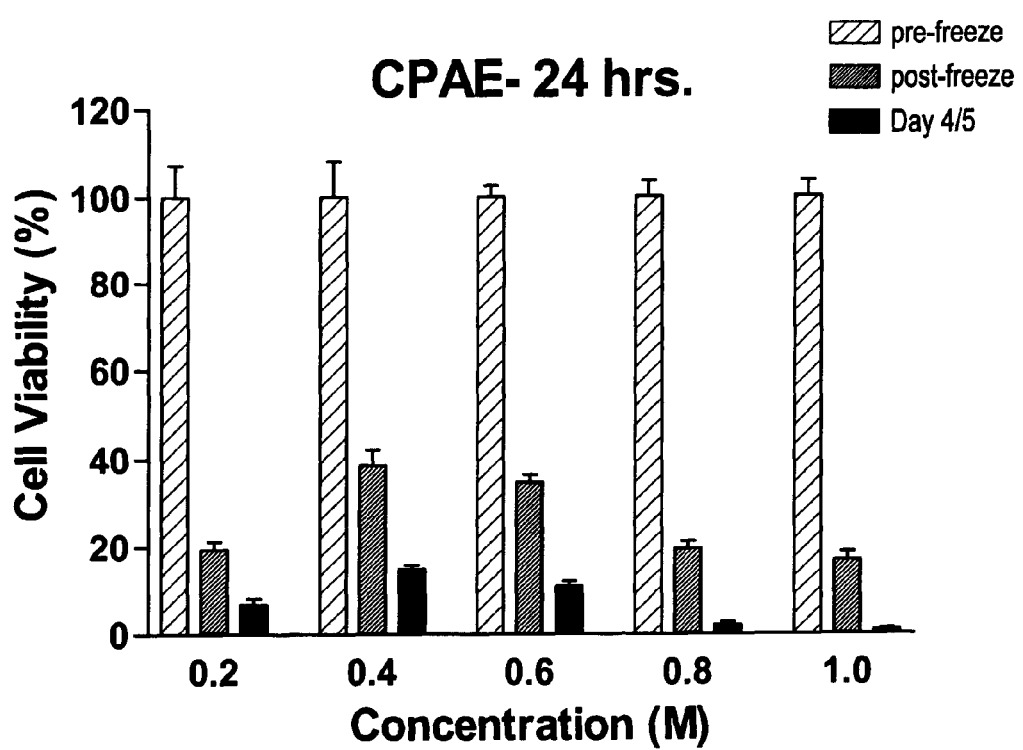
FIG. 6 demonstrates the cell viability before and after freezing where, prior to freezing, the cell line is incubated for 24 hours in a culture medium containing 0.2M trehalose.
Figure 7:
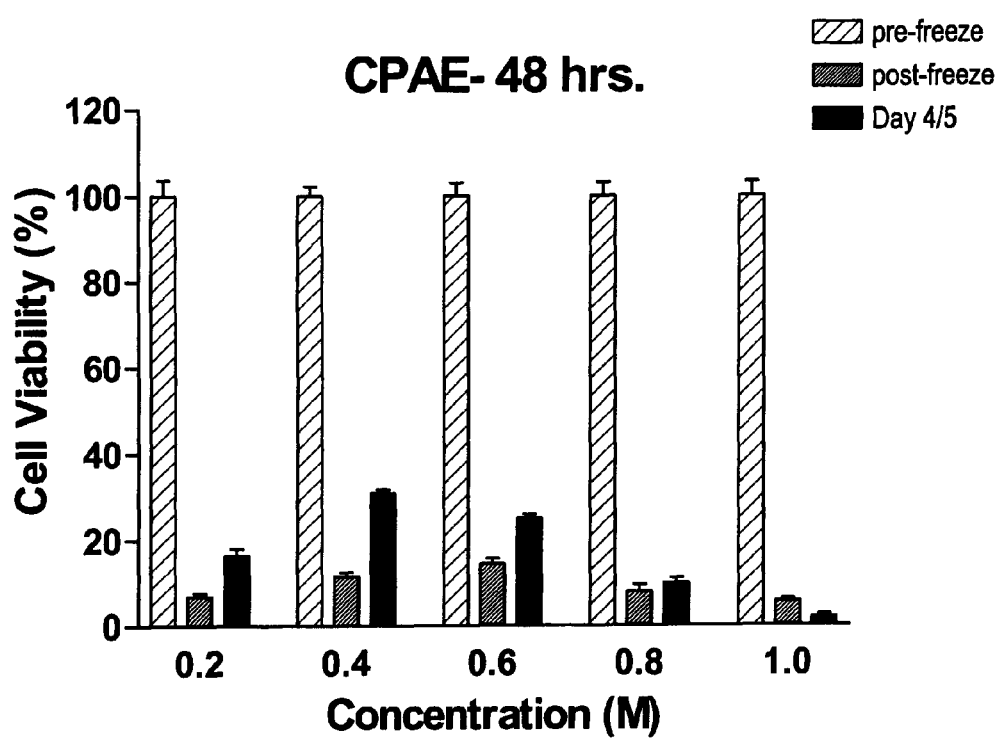
FIG. 7 demonstrates the cell viability before and after freezing where, prior to freezing, the cell line is incubated for 48 hours in a culture medium containing 0.2M trehalose.
Figure 8:
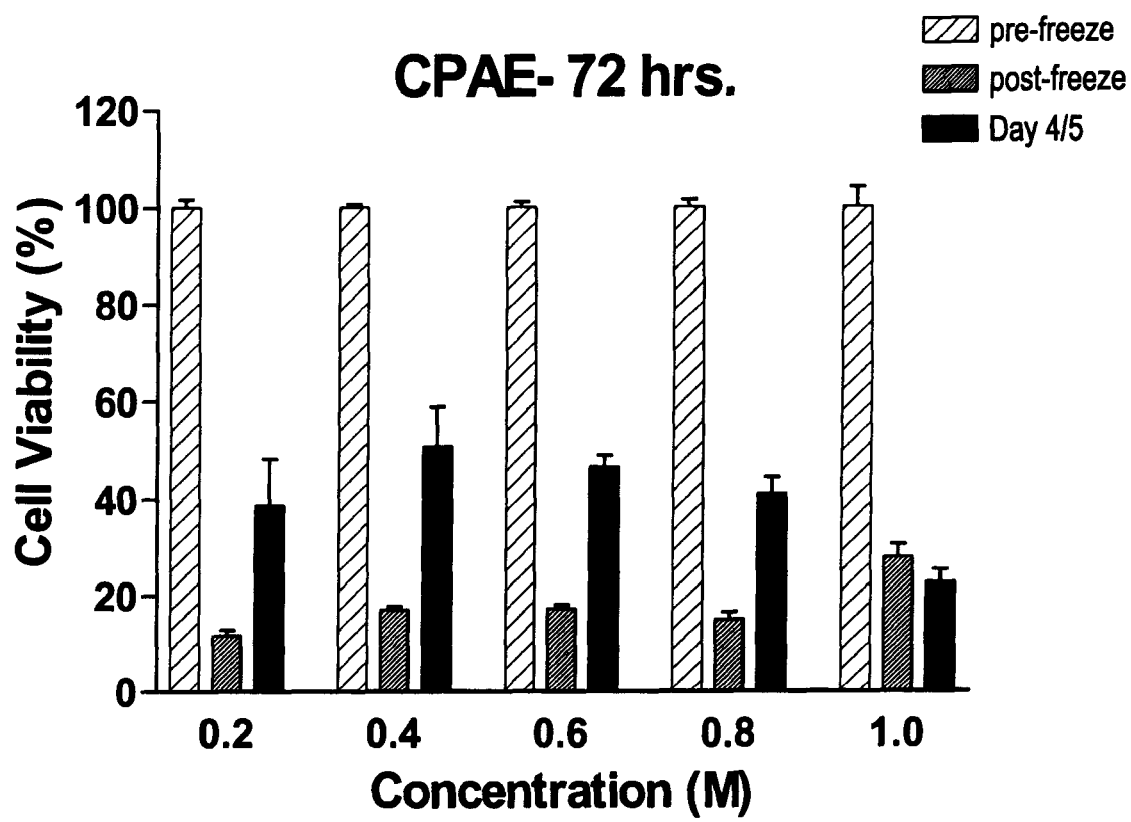
FIG. 8 demonstrates the cell viability before and after freezing where, prior to freezing, the cell line is incubated for 72 hours in a culture medium containing 0.2M trehalose.

Cells are subsequently placed in 0-1.0M trehalose in DMEM (50 µl) and immediately cryopreserved using a controlled-rate freezer at −1.0° C./min. The following day, the cells are thawed by incubation for 30 minutes at −20° C., followed by rapid thawing at 37° C. The trehalose is diluted with 150 µl of DMEM (10% fetal calf serum, FCS) and the cells are left for one hour at 37° C. Cell viability is then reassessed using alamarBlue by incubation for three hours. Cell viability is also assessed on day four or five post-thaw. The results of these experiments are depicted in FIGS. 1-8.

REFERENCES CITED (All of Which are Hereby Incorporated by Reference)

1. Polge C., A. Y. Smith & A. S. Parkes. 1949. Revival of spermatozoa after vitrification and de-hydration at low temperatures. Nature, 164:666.
2. Lovelock J. E. & M. W. H. Bishop. 1959. Prevention of freezing damage to living cells by dimethylsulphoxide. Nature, 183:1394-1395.
3. Brockbank K. G. M. & K. M. Smith. 1993. Synergistic Interaction Of Low-Molecular Weight Polyvinyl-pyrrolidones with Dimethylsulfoxide during Cell Cryopreservation. Transplant Proc. 25:3185-3197.
4. Song Y. C. et al., 2000. Vitreous cryopreservation maintains the function of vascular grafts. Nature Biotechnology, 18:296 -299.
5. Crowe J. H. et al., 1998. The role of vitrification in anhydrobiosis. Ann Rev Physiol. 60: 73-103.
6. Potts M. 1994. Desiccation tolerance of prokaryotes. Microbiol Rev 58: 755-805.
7. Crowe J. H. et al., 1988. Interactions of sugars with membranes. Biochim Biophys Acta 947:367-384.
8. Crowe J. H. et al., 1993. Anhydrobiosis. Ann Rev Physiol, 54:579-599.
9. Bieganski R. M. et al., 1998. Stabilization of active recombinant retroviruses in an amorphous dry state with trehalose. Biotechnol Prog 14:615-620.
10. Womersley C. et al., 1986. Inhibition of dehydration-induced fusion between liposomal membranes by carbohydrates as measured by fluorescence energy-transfer. Cryobiology 23:245-255.
11. Castro, A. G., Lapinski, J., Tunnacliffe, A. Nature Biotechnology 18:473, 2000.
12. Eroglu A et al., 2000. Intracellular trehalose improves the survival of cryopreserved mammalian cells. Nature Biotechnology 18:163-167. U.S. Pat. No. 6,127,777 to Toner et al.
13. Beattie, G. M., Crowe, J. H., Tablin, F., Hayek, A. Cryopreservation of human adult and fetal pancreatic cells and human platelets. U.S. Pat. No. 5,827,741, 1998.
14. Beattie, G. M., Crowe, J. H., Lopez, A. D., Cirulli, V., Ricordi, C., Hayek, A. Trehalose: a cryoprotectant that enhances recovery and preserves function of human pancreatic islets after long-term storage. Diabetes 46:519-523, 1997.
15. Acker, J. P., Toner, M. Tissue Engineering: Biopreservation. Science and Medicine, 126-127, 2002.

What is claimed is:

1. A method for preserving living mammalian cellular material, comprising:
incubating the mammalian cellular material in a culture medium containing at least one sugar for at least three hours; and
after said incubation, subjecting the mammalian cellular material to a preservation protocol selected from the group consisting of freezing, vitrification, freeze-drying and desiccation, wherein:
said culture medium contains from 0.2 to 0.4M sugar,
the at least one sugar comprises trehalose, and
the cellular material is natural or man-made tissue.

2. The method of claim 1, wherein said mammalian cellular material is incubated in said culture medium containing at least one sugar for from 3 to 120 hours.

3. The method of claim 1, wherein said mammalian cellular material is incubated in said culture medium containing at least one sugar for at least 6 hours.

4. The method of claim 1, wherein said mammalian cellular material is incubated in said culture medium containing at least one sugar for at least 12 hours.

5. The method of claim 1, wherein said mammalian cellular material is incubated in said culture medium containing at least one sugar for at least 18 hours.

6. The method of claim 1, wherein said mammalian cellular material is incubated in said culture medium containing at least one sugar for at least 24 hours.

7. The method of claim 1, wherein said mammalian cellular material is incubated in said culture medium containing at least one sugar for at least 48 hours.

8. The method of claim 1, wherein said mammalian cellular material is incubated in said culture medium containing at least one sugar for at least 72 hours.

9. The method of claim 1, wherein said mammalian cellular material is incubated in said culture medium containing at least one sugar for at least 96 hours.

10. The method of claim 1, wherein said preservation protocol comprises at least one of cooling the mammalian cellular material and drying the mammalian cellular material.

11. The method of claim 1, wherein said preservation protocol comprises cooling the mammalian cellular material in said culture medium containing at least one sugar.

12. The method of claim 11, further comprising adding cryoprotectant to said culture medium prior to cooling.

13. The method of claim 12, wherein said cryoprotectant includes at least one sugar.

14. The method of claim 12, wherein said cryoprotectant is selected from the group consisting of acetamide, agarose, alginate, alanine, albumin, ammonium acetate, anti-freeze proteins, butanediol, chondroitin sulfate, chloroform, choline, cyclohexanediols, cyclohexanediones, cyclohexanetriols, dextrans, diethylene glycol, dimethyl acetamide, dimethyl formamide, dimethyl sulfoxide, erythritol, ethanol, ethylene glycol, ethylene glycol monomethyl ether, formamide, glucose, glycerol, glycerophosphate, glyceryl monoacetate, glycine, glycoproteins, hydroxyethyl starch, inositol, lactose, magnesium chloride, magnesium sulfate, maltose, mannitol, mannose, methanol, methoxy propanediol, methyl acetamide, methyl formamide, methyl ureas, methyl glucose, methyl glycerol, phenol, pluronic polyols, polyethylene glycol, polyvinylpyrrolidone, proline, propanediol, pyridine N-oxide, raffinose, ribose, serine, sodium bromide, sodium chloride, sodium iodide, sodium nitrate, sodium nitrite, sodium sulfate, sorbitol, sucrose, trehalose, triethylene glycol, trimethylamine acetate, urea, valine and xylose.

15. The method of claim 1, wherein said culture medium contains 0.2M sugar.

16. The method of claim 1, wherein said preservation protocol comprises cooling said mammalian cellular material in a cryoprotectant-containing solution.

17. The method of claim 16, wherein said cryoprotectant-containing solution comprises at least one sugar.

18. The method of claim 16, wherein said cryoprotectant-containing solution contains at least one cryoprotectant selected from the group consisting of acetamide, agarose, alginate, alanine, albumin, ammonium acetate, anti-freeze proteins, butanediol, chondroitin sulfate, chloroform, choline, cyclohexanediols, cyclohexanediones, cyclohexanetriols, dextrans, diethylene glycol, dimethyl acetamide, dimethyl formamide, dimethyl sulfoxide, erythritol, ethanol, ethylene glycol, ethylene glycol monomethyl ether, formamide, glucose, glycerol, glycerophosphate, glyceryl monoacetate, glycine, glycoproteins, hydroxyethyl starch, inositol, lactose, magnesium chloride, magnesium sulfate, maltose, mannitol, mannose, methanol, methoxy propanediol, methyl acetamide, methyl formamide, methyl ureas, methyl glucose, methyl glycerol, phenol, pluronic polyols, polyethylene glycol, polyvinylpyrrolidone, proline, propanediol, pyridine N-oxide, raffinose, ribose, serine, sodium bromide, sodium chloride, sodium iodide, sodium nitrate, sodium nitrite, sodium sulfate, sorbitol, sucrose, trehalose, triethylene glycol, trimethylamine acetate, urea, valine and xylose.

19. The method of claim 16, wherein said cryoprotectant-containing solution contains 0.1 to 2.0M sugar.

20. The method of claim 19, wherein said cryoprotectant-containing solution contains 0.2 to 0.6M sugar.

* * * * *